(12) United States Patent
Spiridigliozzi et al.

(10) Patent No.: US 7,510,571 B2
(45) Date of Patent: *Mar. 31, 2009

(54) PLEATED COMPOSITE EPTFE/TEXTILE HYBRID COVERING

(75) Inventors: John Spiridigliozzi, Sharon, MA (US); William R. Quinn, Swampscott, MA (US); Ryan Cahill, Holmdel, NJ (US)

(73) Assignee: Boston Scientific, SCIMED, Inc., Maple Grove, MN (US)

( * ) Notice: Subject to any disclaimer, the term of this patent is extended or adjusted under 35 U.S.C. 154(b) by 2 days.

This patent is subject to a terminal disclaimer.

(21) Appl. No.: 10/643,315

(22) Filed: Aug. 19, 2003

(65) Prior Publication Data

US 2004/0033364 A1   Feb. 19, 2004

Related U.S. Application Data

(63) Continuation-in-part of application No. 10/166,842, filed on Jun. 11, 2002.

(60) Provisional application No. 60/297,401, filed on Jun. 11, 2001.

(51) Int. Cl.
*A61F 2/06* (2006.01)
(52) U.S. Cl. .................. 623/1.28; 623/1.13
(58) Field of Classification Search ............. 623/1.28, 623/1.29
See application file for complete search history.

(56) References Cited

U.S. PATENT DOCUMENTS

| 4,082,893 | A |   | 4/1978  | Okita |
|-----------|---|---|---------|-------|
| 4,850,999 | A | * | 7/1989  | Planck ............ 623/1.44 |
| 5,123,917 | A |   | 6/1992  | Lee |
| 5,133,742 | A |   | 7/1992  | Pinchuk |
| 5,229,431 | A |   | 7/1993  | Pinchuk |
| 5,282,847 | A |   | 2/1994  | Trescony et al. |
| 5,549,860 | A |   | 8/1996  | Charlesworth et al. |
| 5,607,464 | A |   | 3/1997  | Trescony et al. |
| 5,628,788 | A | * | 5/1997  | Pinchuk ............ 623/1.2 |
| 5,653,745 | A |   | 8/1997  | Trescony et al. |
| 5,665,114 | A |   | 9/1997  | Weadock et al. |
| 5,693,085 | A |   | 12/1997 | Buirge et al. |
| 5,700,285 | A |   | 12/1997 | Myers et al. |
| 5,723,004 | A |   | 3/1998  | Dereume et al. |
| 5,735,892 | A |   | 4/1998  | Myers et al. |
| 5,749,880 | A |   | 5/1998  | Banas et al. |
| 5,925,075 | A |   | 7/1999  | Myers et al. |
| 5,928,279 | A |   | 7/1999  | Shannon et al. |

(Continued)

FOREIGN PATENT DOCUMENTS

EP   0 666 066 A1   8/1995

(Continued)

*Primary Examiner*—Corrine M McDermott
*Assistant Examiner*—Christopher D Prone
(74) *Attorney, Agent, or Firm*—Hoffmann & Baron, LLP

(57) ABSTRACT

A composite multilayer implantable material having a first inner tubular layer formed of expanded polytetrafluoroethyene having a porous microstructure defined by nodes interconnected by fibrils, wherein said first layer has a plurality of pleated folds, a second tubular layer formed of textile material circumferentially disposed exteriorly to said first layer; and having an elastomeric bonding agent applied to one of said first layer or second layer and disposed within the pores of said microstructure for securing said first layer to said second layer.

32 Claims, 8 Drawing Sheets

Section A-A

U.S. PATENT DOCUMENTS

| | | |
|---|---|---|
| 5,948,018 A | 9/1999 | Dereume et al. |
| 5,976,192 A | 11/1999 | McIntyre et al. |
| 6,001,125 A | 12/1999 | Golds et al. |
| 6,080,198 A | 6/2000 | Lentz et al. |
| 6,096,070 A | 8/2000 | Ragheb et al. |
| 6,165,212 A | 12/2000 | Dereume et al. |
| 6,264,684 B1 * | 7/2001 | Banas et al. ............... 623/1.13 |
| 6,364,903 B2 | 4/2002 | Tseng et al. |
| 6,368,347 B1 | 4/2002 | Maini et al. |
| 6,428,571 B1 | 8/2002 | Lentz et al. |
| 6,440,166 B1 | 8/2002 | Kolluri |
| 6,514,283 B2 | 2/2003 | DiMatteo et al. |
| 6,517,571 B1 | 2/2003 | Brauker et al. |
| 6,524,334 B1 | 2/2003 | Thompson |
| 6,547,815 B2 | 4/2003 | Myers |
| 2001/0049553 A1 | 12/2001 | De Paulis |
| 2003/0082323 A1 | 5/2003 | Venditti et al. |
| 2003/0082324 A1 | 5/2003 | Sogard et al. |

FOREIGN PATENT DOCUMENTS

| | | |
|---|---|---|
| EP | 1 212 988 A2 | 6/2002 |
| WO | WO 02/100454 A1 | 12/2002 |

* cited by examiner

Section A-A

Section B-B

PLEATED COMPOSITE EPTFE/TEXTILE HYBRID COVERING

CROSS-REFERENCE TO RELATED APPLICATIONS

This application is a continuation in part of application Ser. No. 10/166,842, filed Jun. 11, 2002, which claims priority to U.S. Provisional Application No. 60/297,401 filed Jun. 11, 2001, both of which are incorporated by reference herein.

FIELD OF THE INVENTION

The present invention relates generally to a implantable prosthesis material and structure. More particularly, the present invention relates to a composite multilayer implantable material and structure having a textile layer, an expanded polytetrafluoroethylene layer (ePTFE) formed in a pleated configuration and an elastomeric bonding agent layer, which joins the textile and ePTFE layer to form an integral structure.

BACKGROUND OF THE INVENTION

Implantable prostheses are commonly used in medical applications. One of the more common prosthetic structures is a tubular prosthesis which may be used as a vascular graft to replace or repair damaged or diseased blood vessel. To maximize the effectiveness of such a prosthesis, it should be designed with characteristics which closely resemble that of the natural body lumen which it is repairing or replacing.

One form of a conventional tubular prosthesis specifically used for vascular grafts includes a textile tubular structure formed by weaving, knitting, braiding or any non-woven textile technique processing synthetic fibers into a tubular configuration. Tubular textile structures have the advantage of being naturally porous, which allows desired tissue ingrowth and assimilation into the body. This porosity, which allows for ingrowth of surrounding tissue, must be balanced with fluid tightness to minimize leakage during the initial implantation stage.

Attempts to control the porosity of the graft while providing a sufficient fluid barrier have focused on increasing the thickness of the textile structure, providing a tighter stitch construction and incorporating features such as velours to the graft structure. Further, most textile grafts require the application of a biodegradable natural coating, such as collagen or gelatin in order to render the graft blood tight. While grafts formed in this manner overcome certain disadvantages inherent in attempts to balance porosity and fluid tightness, these textile prostheses may exhibit certain undesirable characteristics. These characteristics may include an undesirable increase in the thickness of the tubular structure, which makes implantation more difficult. These textile tubes may also be subject to kinking, bending, twisting or collapsing during handling. Moreover, application of a coating may render the grafts less desirable to handle from a tactility point of view.

It is also well known to form a prosthesis, especially a tubular graft, from polymers such as polytetrafluoroethylene (PTFE). A tubular graft may be formed by stretching and expanding PTFE into a structure referred to as expanded polytetrafluoroethylene (ePTFE). Tubes formed of ePTFE exhibit certain beneficial properties as compared with textile prostheses. The expanded PTFE tube has a unique structure defined by nodes interconnected by fibrils. The node and fibril structure defines micropores, which facilitate a desired degree of tissue ingrowth while remaining substantially fluid-tight. Tubes of ePTFE may be formed to be exceptionally thin and yet exhibit the requisite strength necessary to serve in the repair or replacement of a body lumen. The thinness of the ePTFE tube facilitates ease of implantation and deployment with minimal adverse impact on the body.

While exhibiting certain superior attributes, ePTFE tubes are not without certain disadvantages. Grafts formed of ePTFE tend to be relatively non-compliant as compared with textile grafts and natural vessels. Further, while exhibiting a high degree of tensile strength, ePTFE grafts are susceptible to tearing. Additionally, ePTFE grafts lack the suture compliance of coated textile grafts. This may cause undesirable bleeding at the suture hole. Thus, the ePTFE grafts lack many of the advantageous properties of certain textile grafts.

It is also known that it is extremely difficult to join PTFE and ePTFE to other materials via adhesives or bonding agents due to its chemically inert and non-wetting character. Wetting of the surface by the adhesive is necessary to achieve adhesive bonding, and PTFE and ePTFE are extremely difficult to wet without destroying the chemical properties of the polymer. Thus, heretofore, attempts to bond ePTFE to other dissimilar materials such as textiles have been difficult.

It is also known to use vascular grafts in conjunction with support structures. Such support structures typically come in the form of stents, which are formed of metal or polymeric materials generally formed in a tubular structure and are used to hold a vein or artery open. Stents are well known in the art and may be self-expanding or radially expandable by balloon expansion. Examples of stent/graft configurations known in the art can be seen in U.S. Pat. Nos. 5,700,285; 5,749,880; and 5,123,917, each of which are herein incorporated by reference. It is advantageous to use stent/graft configurations because the stent provides and ensures the patency of the prosthesis, while the vascular graft provides biocompatible properties in a vessel more suitable for blood to flow.

While using a vascular graft in conjunction with support structures offers certain benefits, it is also known that support structures such as a stent can result in axial elongation and radial shrinkage of the graft material due to the stresses applied to the graft material by the support structure during the contraction and expansion of the support structure.

It is apparent that conventional textile prostheses as well as ePTFE prostheses have acknowledged advantages and disadvantages. Neither of the conventional prosthetic materials exhibits fully all of the benefits desirable for use as a vascular prosthesis.

It is therefore desirable to provide an implantable material and structure, preferably in the form of a tubular vascular prosthesis, which achieves many of the above-stated benefits without the resultant disadvantages associated therewith.

SUMMARY OF THE INVENTION

The present invention provides a composite multi-layered implantable prosthetic material and structure, which may be used in various applications, especially vascular applications. The implantable structure of the present invention may include a pleated ePTFE-lined textile graft, a pleated ePTFE graft, covered with a textile covering. Moreover, additional ePTFE layers may be combined with any of these embodiments.

In accordance with the present invention, pleats are provided along the length of the implantable material and structure. The number and length of the pleated sections can vary to control the resultant axial elongation, plastic deformation, longitudinal foreshortening and radial shrinkage of the graft material due to the stresses applied to the graft material by the support structure during the contraction and expansion of the support structure.

The composite multi-layered implantable structure of the present invention includes a first layer formed of a textile material and a second layer formed of expanded polytetrafluoroethylene (ePTFE) being layered in a pleated pattern having a porous microstructure defined by nodes interconnected by fibrils. An elastomeric bonding agent may be applied to the second layer and disposed within the pores of the microstructure for securing the first layer to the second layer.

In another embodiment, the composite multi-layered implantable structure of the present invention may have a first inner tubular layer and a second outer tubular layer, both formed of ePTFE having a porous microstructure defined by nodes interconnected by fibrils. The first and second layers of ePTFE also may have a support structure positioned therebetween. Typically, this support structure takes the form of a radially expandable member, preferably a stent. A third tubular layer formed of textile material may be circumferentially disposed exteriorly to the first and second layers, and an elastomeric bonding agent may be applied to the second layer of ePTFE or the textile layer, and disposed within the pores of the ePTFE microstructure when the layers are bonded together. The bonding agent helps secure the second outer layer of ePTFE to the third textile layer.

In another embodiment, the multi-layered implantable structure further comprises a fourth layer of textile material circumferentially disposed interior to said first and second ePTFE layer and bonded to the first ePTFE layer with the elastomeric bonding agent. It is contemplated to further secure additional layers either interior or exterior said composite structure. The first and second ePTFE layers are preferably pleated in the axial direction prior to the bonding step.

The bonding agent may be selected from a group of materials including biocompatible elastomeric materials such as urethanes, silicones, isobutylene/styrene copolymers, block polymers, and combinations thereof.

The tubular composite material and structure of the present invention may also be formed from appropriately layered sheets which can then be overlapped to form tubular structures. Bifurcated, tapered, conical, and stepped-diameter tubular structures may also be formed from the present invention. The layered sheets may be pleated after being formed into a tubular structure.

The textile layer may be formed of various textiles including knits, weaves, stretch knits, braids, any non-woven processing techniques, and combinations thereof. Various biocompatible polymeric materials may be used to form the textile structures, including polyethylene terephthalate (PET), naphthalene dicarboxylate derivatives such as polyethylene naphthalate, polybutylene naphthalate, polytrimethylene naphthalate, trimethylenediol naphthalate, ePTFE, natural silk, polyethylene and polypropylene, among others. PET is a particularly desirable material for forming the textile layer.

The bonding agent is applied in solution to one surface of the ePTFE layer, preferably by spray coating. The textile layer is then placed in contact with the coated surface of the ePTFE layer. The bonding agent may also be applied in powder form by any known techniques; e.g. electrostatic spray. The bonding agent may also be applied and activated by thermal and/or chemical processes well known in the art and may be disposed within the pores of the coated surface.

The present invention also provides an ePTFE-lined textile graft. The lined textile graft includes a tubular textile substrate bonded using a biocompatible elastomeric material to a tubular liner of ePTFE. A coating of an elastomeric bonding agent may be applied to the surface of the ePTFE liner so that the bonding agent is present in the micropores thereof. The coated liner is then secured to the tubular textile structure via the elastomeric bonding agent. The liner and textile graft can each be made very thin and still maintain the advantages of both types of materials.

The present invention further provides a textile-covered ePTFE graft. The tubular ePTFE graft structure includes micropores defined by nodes interconnected by fibrils. A coating of an elastomeric bonding agent is applied to the surface of the ePTFE tubular structure with the bonding agent being resident within the microporous structure thereof. A tubular textile structure is applied to the coated surface of the ePTFE tubular structure and secured thereto by the elastomeric bonding agent.

The composite multi-layered implantable structures of the present invention are designed to take advantage of the inherent beneficial properties of the materials forming each of the layers. The textile layer provides for enhanced tissue ingrowth, high suture retention strength and longitudinal compliance for ease of implantation. The ePTFE layer provides the beneficial properties of sealing the textile layer without need for coating the textile layer with a sealant such as collagen. The sealing properties of the ePTFE layer allow the wall thickness of the textile layer to be minimized. Further, the ePTFE layer exhibits enhanced thrombo-resistance upon implantation. Moreover, the elastomeric bonding agent not only provides for an integral composite structure, but adds further puncture-sealing characteristics to the final prosthesis. Additionally, plastic deformation of the ePTFE layer is controlled by the pleated structure, therefore detrimental effects on the beneficial properties of the ePTFE are minimized.

In further aspects of the invention, the implantable structure may be used in conjunction with radially-expandable members such as stents and other structures which are capable of maintaining patency of the implantable structure in a bodily vessel. For example, a stent may be disposed between two ePTFE layers with the outer ePTFE layer being joined to a tubular textile structure via the elastomeric bonding agent. Optionally, a textile reinforcement may be secured to the inner ePTFE layer via the elastomeric bonding agent, in addition to or in the alternative the outer tubular textile structure. Any stent construction known to those skilled in the art may be used, including self-expanding stents, as well as, balloon-expandable stents.

Therefore, in accordance with the present invention, there is provided a composite multilayer implantable material having a first inner tubular layer formed of expanded polytetrafluoroethyene having a porous microstructure defined by nodes interconnected by fibrils, wherein said first layer has a plurality of pleated folds, a second tubular layer formed of textile material circumferentially disposed exteriorly to said first layer; and having an elastomeric bonding agent applied to one of said first layer or second layer and disposed within the pores of said microstructure for securing said first layer to said second layer.

In accordance with even further embodiment of the present invention, a method for producing a graft having pleated regions along it length is provided. The method includes forming a textile ePTFE composite graft material by providing a first tubular ePTFE structure having a microporous structure of nodes interconnected by fibrils, providing a second tubular ePTFE structure having a microporous structure of nodes interconnected by fibrils, folding a plurality of pleats into said first tubular ePTFE structure and said second tubular ePTFE structure, providing a tubular textile structure, placing a tubular support structure circumferentially around said first ePTFE tubular structure, placing said second tubular ePTFE structure circumferentially around said tubular support structure, applying a coating of an elastomeric bonding graft to a surface of said second ePTFE structure or said textile structure; and securing said coated liner surface to said textile structure.

Various additives such as drugs, growth-factors, anti-thrombogenic agents and the like may also be employed.

Figure 1:
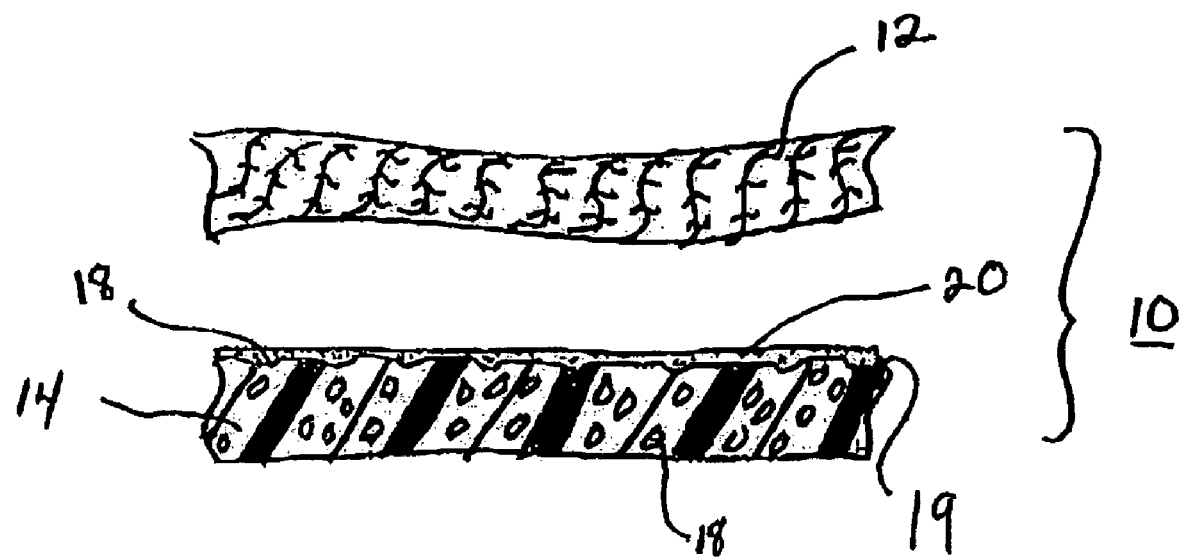
FIG. 1 shows a schematic cross-section, a portion of a composite multi-layered implantable structure of the present invention.

DETAILED DESCRIPTION OF THE PREFERRED EMBODIMENT:

The present invention provides a composite implantable prosthesis material and structure, desirably a vascular prosthesis material includes two layers of ePTFE, typically surrounding a stent, and a layer of a textile material. The ePTFE stent/graft layers are secured together, with the textile layer, by an elastomeric bonding agent. The vascular prosthesis material and vascular prosthesis of the present invention may include an ePTFE-lined textile vascular graft, and a ePTFE vascular graft including a textile covering. While this invention is satisfied by embodiments in many different forms, there are shown in the drawings and herein described in detail, embodiments of the invention with the understanding that the present disclosure is to be considered as exemplary of the principles of the present invention and is not intended to limit the scope of the invention to the embodiments illustrated. In this disclosure, the material and structure of the present invention may be described with respect to its application in the structure of a graft or stent-graft prosthesis device.

Referring to FIG. 1, a schematic cross-section of a portion of an embodiment of the vascular prosthesis material 10 is shown. As noted above, the material 10 may be a portion of a graft, or any other implantable structure.

The material 10 includes a first layer 12, which is formed of a textile material. The textile material 12 of the present invention may be formed from synthetic yarns that may be flat, shaped, twisted, textured, pre-shrunk or un-shrunk. Preferably, the yarns are made from thermoplastic materials including, but not limited to, polyesters, polypropylenes, polyethylenes, polyurethanes, polynaphthalenes, polytetrafluoroethylenes and the like. The yarns may be of the multifilament, monofilament or spun types. In most vascular applications, multifilaments are preferred due to the increase in flexibility. Where enhanced crush resistance is desired, the use of monofilaments have been found to be effective. As is well known, the type and denier of the yarn chosen are selected in a manner which forms a pliable soft tissue prosthesis and, more particularly, a vascular structure have desirable properties.

The material 10 further includes a second layer 14 formed of expanded polytetrafluoroethylene (ePTFE). The ePTFE layer 14 may be produced from the expansion of PTFE formed in a paste extrusion process. The PTFE extrusion may be expanded and sintered in a manner well known in the art to form ePTFE having a microporous structure defined by nodes interconnected by elongate fibrils. The distance between the nodes, referred to as the internodal distance (IND), may be varied by the parameters employed during the expansion and sintering process. The resulting process of expansion and sintering yields pores 18 within the structure of the ePTFE layer. The size of the pores are defined by the IND of the ePTFE layer.

The ePTFE of the present invention may also be "ultrathin" ePTFE as described in commonly-owned applications, U.S. Ser. Nos. 10/012,825 and 10/012,919, the disclosures of which are herein incorporated by reference.

The composite material 10 of the present invention may further include a bonding agent 20 applied to one surface 19 of ePTFE layer 18. The bonding agent 20 is preferably applied in solution by a spray coating process. However, other processes may be employed to apply the bonding agent.

In the present invention, the bonding agent may include various biocompatible, elastomeric bonding agents such as urethanes, styrene/isobutylene/styrene block copolymers (SIBS), silicones, and combinations thereof. Other similar materials are contemplated. Most desirably, the bonding agent may include polycarbonate urethanes identified by the trade name CORETHANE®. This urethane is provided as an adhesive solution with preferably 7.5% Corethane, 2.5, in dimethylacetamide (DMAc) solvent.

The term "elastomeric" as used herein refers to a substance having the characteristic that it tends to resume an original shape after any deformation thereto, such as stretching, expanding, or compression. It also refers to a substance which has a non-rigid structure, or flexible characteristics in that it is not brittle, but rather has compliant characteristics contributing to its non-rigid nature.

The polycarbonate urethane polymers particularly useful in the present invention are more fully described in U.S. Pat. Nos. 5,133,742 and 5,229,431, which are incorporated in their entirety herein by reference. These polymers are particularly resistant to degradation in the body over time and exhibit exceptional resistance to cracking in vivo. These polymers are segmented polyurethanes which employ a combination of hard and soft segments to achieve their durability, biostability, flexibility and elastomeric properties.

The polycarbonate urethanes useful in the present invention are prepared from the reaction of an aliphatic or aromatic polycarbonate macroglycol and a diisocyanate in the presence of a chain extender. Aliphatic polycarbonate macroglycols such as polyhexane carbonate macroglycols and aromatic diisocyanates such as methylene diisocyanate are most desired due to the increased biostability, higher intramolecular bond strength, enhanced heat stability and flex fatigue life, as compared to other materials.

The polycarbonate urethanes particularly useful in the present invention are the reaction products of a macroglycol, a diisocyanate and a chain extender.

A polycarbonate component is characterized by repeating

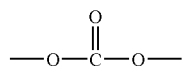

units, and a general formula for a polycarbonate macroglycol is as follows:

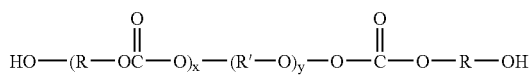

wherein x is from 2 to 35, y is 0, 1 or 2, R either is cycloaliphatic, aromatic or aliphatic having from about 4 to about 40 carbon atoms or is alkoxy having from about 2 to about 20 carbon atoms, and wherein R' has from about 2 to about 4 linear carbon atoms with or without additional pendant carbon groups.

Examples of typical aromatic polycarbonate macroglycols include those derived from phosgene and bisphenol A or by ester exchange between bisphenol A and diphenyl carbonate such as (4,4'-dihydroxy-diphenyl-2,2'-propane) shown below, wherein n is between about 1 and about 12.

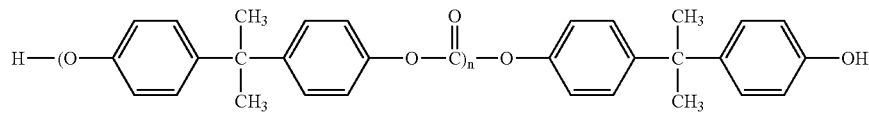

Typical aliphatic polycarbonates are formed by reacting cycloaliphatic or aliphatic diols with alkylene carbonates as shown by the general reaction below:

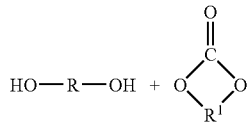

wherein R is cyclic or linear and has between about 1 and about 40 carbon atoms and wherein R1 is linear and has between about 1 and about 4 carbon atoms.

Typical examples of aliphatic polycarbonate diols include the reaction products of 1,6-hexanediol with ethylene carbonate, 1,4-butanediol with propylene carbonate, 1,5-pentanediol with ethylene carbonate, cyclohexanedimethanol with ethylene carbonate and the like and mixtures of above such as diethyleneglycol and cyclohexanedimethanol with ethylene carbonate.

When desired, polycarbonates such as these can be copolymerized with components such as hindered polyesters, for example phthalic acid, in order to form carbonate/ester copolymer macroglycols. Copolymers formed in this manner can be entirely aliphatic, entirely aromatic, or mixed aliphatic and aromatic. The polycarbonate macroglycols typically have a molecular weight of between about 200 and about 4000 Daltons.

Diisocyanate reactants according to this invention have the general structure OCN—R'—NCO, wherein R' is a hydrocarbon that may include aromatic or nonaromatic structures, including aliphatic and cycloaliphatic structures. Exemplary isocyanates include the preferred methylene diisocyanate (MDI), or 4,4-methylene bisphenyl isocyanate, or 4,4'-diphenylmethane diisocyanate and hydrogenated methylene diisocyanate (HMDI). Other exemplary isocyanates include hexamethylene diisocyanate and other toluene diisocyanates such as 2,4-toluene diisocyanate and 2,6-toluene diisocyanate, 4,4' tolidine diisocyanate, m-phenylene diisocyanate, 4-chloro-1,3-phenylene diisocyanate, 4,4-tetramethylene diisocyanate, 1,6-hexamethylene diisocyanate, 1,10-decamethylene diisocyanate, 1,4-cyclohexylene diisocyanate, 4,4'-methylene bis (cyclohexylisocyanate), 1,4-isophorone diisocyanate, 3,3'-dimethyl-4,4'-diphenylmethane diisocyanate, 1,5-tetrahydronaphthalene diisocyanate, and mixtures of such diisocyanates. Also included among the isocyanates applicable to this invention are specialty isocyanates containing sulfonated groups for improved hemocompatibility and the like.

Suitable chain extenders included in this polymerization of the polycarbonate urethanes should have a functionality that is equal to or greater than two. A preferred and well-recognized chain extender is 1,4-butanediol. Generally speaking, most diols or diamines are suitable, including the ethylenediols, the propylenediols, ethylenediamine, 1,4-butanediamine methylene dianiline heteromolecules such as ethanolamine, reaction products of said diisocyanates with water and combinations of the above.

The polycarbonate urethane polymers according to the present invention should be substantially devoid of any significant ether linkages (i.e., when y is 0, 1 or 2 as represented in the general formula hereinabove for a polycarbonate macroglycol), and it is believed that ether linkages should not be present at levels in excess of impurity or side reaction concentrations. While not wishing to be bound by any specific theory, it is presently believed that ether linkages account for much of the degradation that is experienced by polymers not in accordance with the present invention due to enzymes that are typically encountered in vivo, or otherwise, attack the ether linkage via oxidation. Live cells probably catalyze degradation of polymers containing linkages. The polycarbonate urethanes useful in the present invention avoid this problem.

Because minimal quantities of ether linkages are unavoidable in the polycarbonate producing reaction, and because these ether linkages are suspect in the biodegradation of polyurethanes, the quantity of macroglycol should be minimized to thereby reduce the number of ether linkages in the polycarbonate urethane. In order to maintain the total number of equivalents of hydroxyl terminal groups approximately equal to the total number of equivalents of isocyanate terminal groups, minimizing the polycarbonate soft segment necessitates proportionally increasing the chain extender hard segment in the three component polyurethane system. Therefore, the ratio of equivalents of chain extender to macroglycol should be as high as possible. A consequence of increasing this ratio (i.e., increasing the amount of chain extender with respect to macroglycol) is an increase in hardness of the polyurethane. Typically, polycarbonate urethanes of hardnesses, measured on the Shore scale, less than 70 A show small amounts of biodegradation. Polycarbonate urethanes of Shore 75 A and greater show virtually no biodegradation.

The ratio of equivalents of chain extender to polycarbonate and the resultant hardness is a complex function that includes the chemical nature of the components of the urethane system and their relative proportions. However, in general, the hardness is a function of the molecular weight of both chain extender segment and polycarbonate segment and the ratio of equivalents thereof. Typically, the 4,4'-methylene bisphenyl diisocyanate (MDI) based systems, a 1,4-butanediol chain extender of molecular weight 90 and a polycarbonate urethane of molecular weight of approximately 2000 will require a ratio of equivalents of at least about 1.5 to 1 and no greater than about 12 to 1 to provide non-biodegrading polymers. Preferably, the ratio should be at least about 2 to 1 and less than about 6 to 1. For a similar system using a polycarbonate glycol segment of molecular weight of about 1000, the preferred ration should be at least about 1 to 1 and no greater than about 3 to 1. A polycarbonate glycol having a molecular weight of about 500 would require a ratio in the range of about 1.2 to about 1.5:1.

The lower range of the preferred ratio of chain extender to macroglycol typically yields polyurethanes of Shore 80 A hardness. The upper range of ratios typically yields polycarbonate urethanes on the order of Shore 75 D. The preferred elastomeric and biostable polycarbonate urethanes for most medical devices would have a Shore hardness of approximately 85 A.

Generally speaking, it is desirable to control somewhat the cross-linking that occurs during polymerization of the polycarbonate urethane polymer. A polymerized molecular weight of between about 80,000 and about 200,000 Daltons, for example on the order of about 120,000 Daltons (such molecular weights being determined by measurement according to the polystyrene standard), is desired so that the resultant polymer will have a viscosity at a solids content of 43% of between about 900,000 and about 1,800,000 centipoise, typically on the order of about 1,000,000 centipoise. Cross-linking can be controlled by avoiding an isocyanate-rich situation. Of course, the general relationship between the isocyanate groups and the total hydroxyl (and/or amine) groups of the reactants should be on the order of approximately 1 to 1. Cross-linking can be controlled by controlling the reaction temperatures and shading the molar ratios in a direction to be certain that the reactant charge is not isocyanate-rich; alternatively a termination reactant such as ethanol can be included in order to block excess isocyanate groups which could result in cross-linking which is greater than desired.

Concerning the preparation of the polycarbonate urethane polymers, they can be reacted in a single-stage reactant charge, or they can be reacted in multiple states, preferably in two stages, with or without a catalyst and heat. Other components such as antioxidants, extrusion agents and the like can be included, although typically there would be a tendency and preference to exclude such additional components when a medical-grade polymer is being prepared.

Additionally, the polycarbonate urethane polymers can be polymerized in suitable solvents, typically polar organic solvents in order to ensure a complete and homogeneous reaction. Solvents include dimethylacetamide, dimethylformamide, dimethylsulfoxide toluene, xylene, m-pyrrol, tetrahydrofuran, cyclohexanone, 2-pyrrolidone, and the like, or combinations thereof. These solvents can also be used to delivery the polymers to the ePTFE layer of the present invention.

A particularly desirable polycarbonate urethane is the reaction product of polyhexamethylenecarbonate diol, with methylene bisphenyl diisocyanate and the chain extender 1,4-butanediol.

The use of the elastomeric bonding agent in solution is particularly beneficial in that by coating the surface 19 of ePFTE layer 14, the bonding agent solution enters the pores 18 of layer 14 defined by the IND of the ePTFE layer. As the ePTFE is a highly hydrophobic material, it is difficult to apply a bonding agent directly to the surface thereof. By providing a bonding agent which may be disposed within the micropores of the ePFTE structure, enhanced bonding attachment between the bonding agent and the ePFTE surface is achieved.

The bonding agents of the present invention, particularly the materials noted above and, more particularly, polycarbonate urethanes, such as those formed from the reaction of alphatic macroglycols and aromatic or aliphatic diisocyanates, are elastomeric materials which exhibit elastic properties. Conventional ePTFE is generally regarded as an inelastic material, i.e., even though it can be further stretched, it has little memory. Therefore, conventional ePTFE exhibits a relatively low degree of longitudinal compliance. Also, suture holes placed in conventional ePTFE structures do not self-seal, due to the inelasticity of the ePTFE material. By applying an elastomeric coating to the ePTFE structure, both longitudinal compliance and suture hole sealing are enhanced.

Referring again to FIG. 1, textile layer 12 is secured to surface 19 of ePTFE layer 14 which has been coated with bonding agent 20. The textile layer 12 is secured by placing it in contact with the bonding agent. As it will be described in further detail hereinbelow, this process can be performed either by mechanical, chemical, or thermal techniques or combinations thereof.

The composite material 10 may be used in various vascular applications in planar form or in tubular form as a graft. The textile surface may be designed as a tissue contacting surface in order to promote enhanced cellular ingrowth which contributes to the long term patency of the prosthesis. The ePFTE surface 14 may be used as a blood contacting surface so as to minimize leakage and to provide a generally anti-thrombogetic surface. While this is the preferred usage of the composite prosthesis of the prevent invention, in certain situations, the layers may be reversed where indicated.

The present invention provides for various embodiments of composite ePTFE/textile prosthesis.

The composite ePTFE-lined textile graft is desirably formed as follows. A thin ePFTE tube is formed in a conventional forming process such as by tubular extrusion or by sheet extrusion where the sheet is formed into a tubular configuration. The ePTFE tube is placed over a stainless steel mandrel and the ends of the tube are secured. The ePTFE sheet or tube is pleated on the mandrel in a plurality of locations by folding the ePTFE layer over upon itself. The ePTFE tube is then spray coated with an adhesive solution of anywhere from 1%-15% Corethane® urethane, 2.5 in DMAc. As noted above, other adhesive solutions may also be employed. The coated ePTFE tube is placed in an oven heated in a range from 18° C. to 150° C. oven for 5 minutes to overnight to dry off the solution. If desired, the spray coating and drying process can be repeated multiple times to add more adhesive to the ePTFE tube. The pleated regions of the ePTFE layer effectively mask portions of the tubular layer, preventing the adhesive from covering all of the tubing. The coated ePTFE tube is then covered with the textile tube to form the composite prosthesis. One or more layers of elastic tubing, preferably silicone, is then placed over the composite structure. This holds the composite structure together and assures that complete contact and adequate pressure is maintained for bonding purposes. The assembly of the composite graft within the elastic tubing is placed in an oven and heated in a range of 180°-220° C. for approximately 5-30 minutes to bond the layers together.

Thereafter, the ePTFE lined textile graft may be crimped along the tubular surface thereof to impart longitudinal compliance, kink resistance and enhanced handling characteristics. The crimp may be provided by placing a coil of metal or plastic wire around a stainless steel mandrel. The graft is slid over the mandrel and the coil wire. Another coil is wrapped around the assembly over the graft to fit between the spaces of the inner coil. The assembly is then heat set and results in the formation of the desired crimp pattern. It is further contemplated that other conventional crimping processes may also be used to impart a crimp to the ePTFE textile graft.

In order to further enhance the crush and kink resistance of the graft, the graft can be wrapped with a polypropylene monofilament. This monofilament is wrapped in a helical configuration and adhered to the outer surface of the graft either by partially melting the monofilament to the graft or by use of an adhesive.

The ePTFE-lined textile graft exhibits advantages over conventional textile grafts in that the ePTFE liner acts as a barrier membrane which results in less incidences of bleeding without the need to coat the textile graft in collagen. The wall thickness of the composite structure may be reduced while still maintaining the handling characteristics, especially where the graft is crimped. A reduction in suture hole bleeding is seen in that the elastic bonding agent used to bond the textile to the ePTFE, renders the ePTFE liner self-sealing.

The process for forming the textile covered ePTFE vascular graft may be described as follows.

An ePTFE tube formed preferably by tubular paste extrusion is placed over a stainless steel mandrel. After being placed on the mandrel, the ePTFE is pleated in a plurality of locations. The pleats are formed by folding the ePTFE layer over itself, creating a gathered section of ePTFE material. The gathered sections lengthen the amount of ePTFE material used to form the tube. After pleating, the ends of the ePTFE tube are secured. The ePTFE tube is coated using an adhesive solution of from 1%-15% Corethane®, 2.5 in DMAc. The coated ePTFE tubular structure is then placed in an oven heated in a range from 18° C. to 150° C. for 5 minutes to overnight to dry off the solution. The coating and drying process can be repeated multiple times to add more adhesive to the ePTFE tubular structure. The pleats are folded perpendicular to the axial length of the tube, such that longitudinal expansion of the graft device will cause the pleats to unfold.

Once dried, the ePTFE tubular structure may be longitudinally compressed in the axial direction to between 1% to 85% of its length to relax the fibrils of the ePTFE. The amount of desired compression may depend upon the amount of longitudinal expansion that was imparted to the base PTFE green tube to create the ePTFE tube. Longitudinal expansion and compression may be balanced to achieve the desired properties. This is done to enhance the longitudinal stretch properties of the resultant graft. The longitudinal compression process can be performed either by manual compression or by thermal compression. Furthermore, the number and length of the pleated regions of the ePTFE layer, are additional factors that can be modified to alter the properties of the resultant graft.

The compressed ePTFE tube is then covered with a thin layer of the textile tube. One or more layers of elastic tubing, preferably silicone, is placed over the composite. This holds the composite together and assures that there is complete contact and adequate pressure. The assembly is then placed in a 205° C. oven for approximately 10-20 minutes to bond the layers together.

The composite graft can be wrapped with a polypropylene monofilament which is adhered to the outer surface by melting or use of an adhesive. The polypropylene monofilament will increase the crush and kink resistance of the graft. Again, the graft can be crimped in a convention manner to yield a crimped graft.

The textile covered ePTFE graft exhibits superior longitudinal strength as compared with conventional ePTFE vascular grafts. The composite structure maintains high suture retention strength and reduced suture hole bleeding. This is especially beneficial when used as a dialysis access graft in that the composite structure has increased strength and reduced puncture bleeding. This is achieved primarily by the use of an elastomeric bonding agent between the textile tubular structure and the ePTFE tubular structure in which the elastic bonding agent has a tendency to self-seal suture holes.

Figure 2:
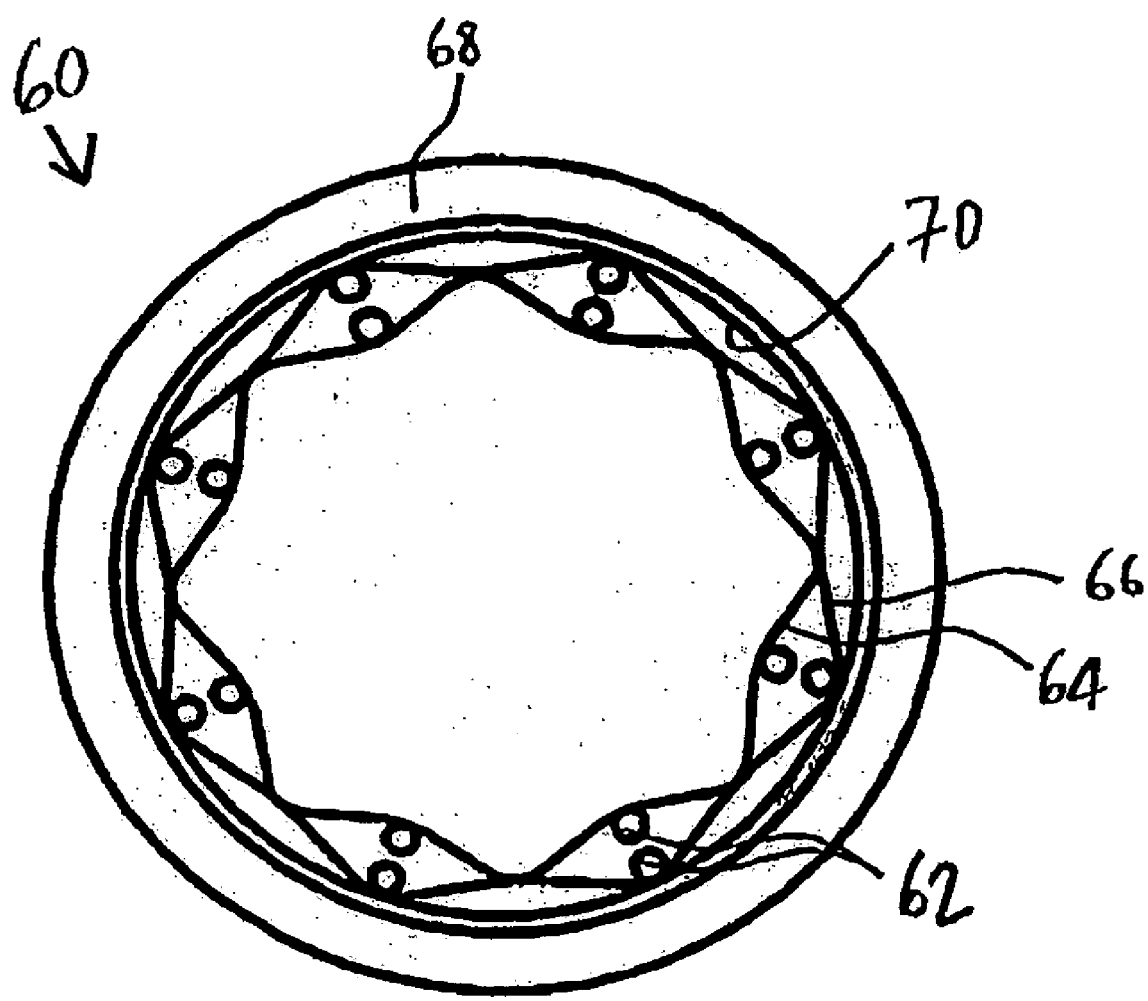
FIG. 2 shows a schematic cross-section of an embodiment of the present invention.
Figure 3:
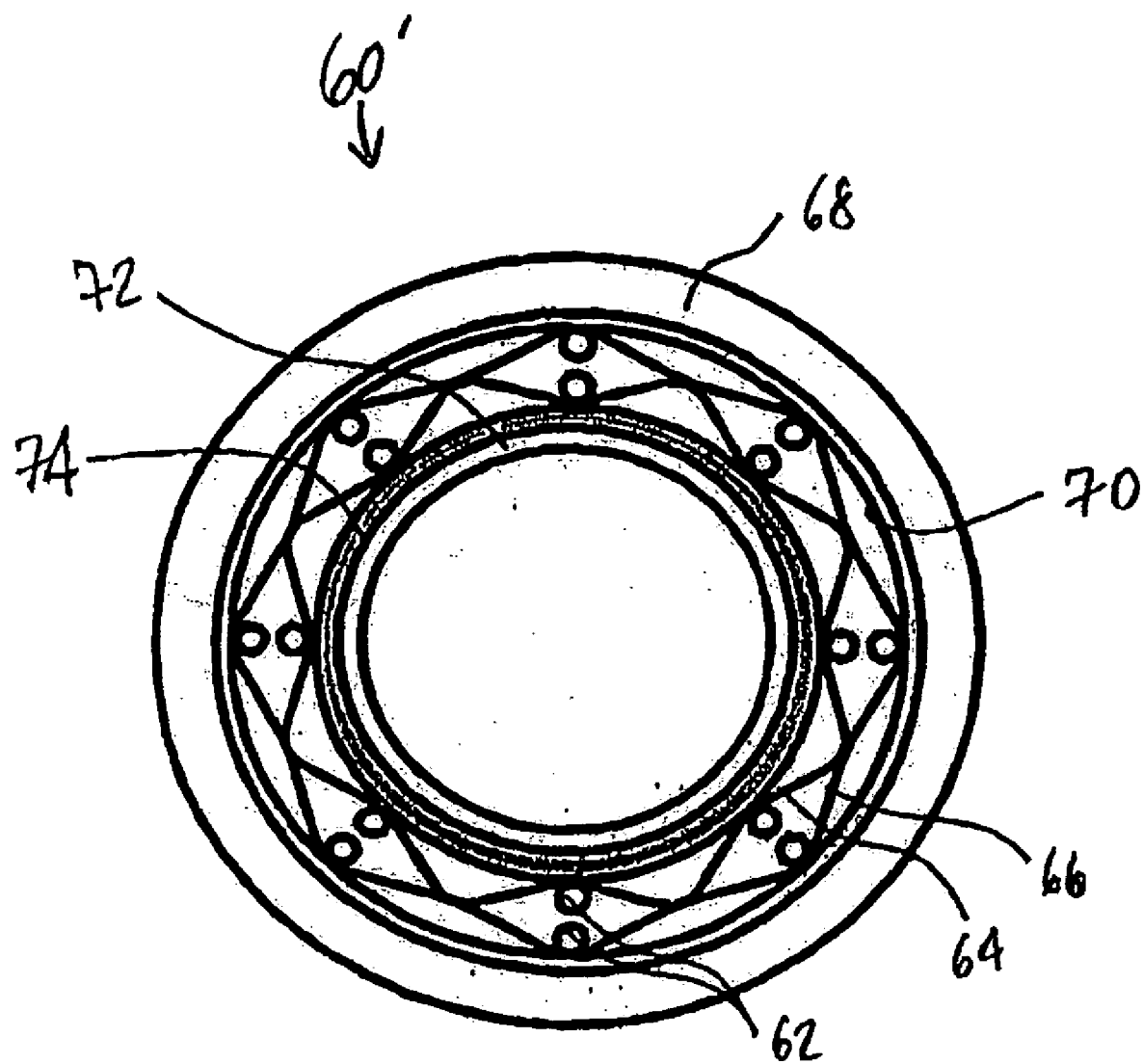
FIG. 3 shows a schematic cross-section of an embodiment of the present invention.

With reference to FIGS. 2 and 3, various embodiments of a multi-layered composite graft of the present invention are depicted. With reference to FIG. 2, a composite graft 60 is shown having a tubular support structure 62 interposed between inner and outer ePTFE layers 64 and 66. The ePTFE layers 64 and 66 are joined using any technique known to those skilled in the art, such as by sintering or with an adhesive (thermoplastic fluoropolymer adhesive (FEP)). The ePTFE layers 64, 66 are joined through interstices found in the support structure 62, preferably without being affixed to the support structure 62. The outer ePTFE layer 66 is bonded to a textile layer 68 with a layer of bonding agent 70. The arrangement of the layers may be altered, wherein the support structure 62 and the ePTFE layers 64, 66 may be disposed externally of the textile layer 68 with the layer of bonding agent 70 being interposed between the textile layer 68 and the inner ePTFE layer 64. The composite graft is formed to allow for simultaneous radial expansion of the support structure 62 along with the ePTFE layers 64, 66 and the textile layer 68. The radial expansion is preferably unhindered by any of the constituent elements of the composite graft.

The tubular support structure 62 may be any structure known in the art, which is capable of maintaining patency of the composite graft 60 in a bodily vessel. For example, the support structure 62 may be a stent, and preferably is radially expandable. Radially expandable member 62 may be of any stent configuration known to those skilled in the art, including those used alone or in a stent/graft arrangement. Various stent types and stent constructions may be employed in the present invention including, without limitation, self-expanding stents and balloon expandable stents. The stents may be capable of radially contracting as well. Self-expanding stents include those that have a spring-like action, which cause the stent to radially expand, or stents, which expand due to the memory properties of the stent material for a particular configuration at a certain temperature. Nitinol® is an example of a material, which may be used as a self-expanding stent. Other materials are of course contemplated, such as stainless steel, platinum, gold, titanium, tantalum, niobium, and other biocompatible materials, as well as polymeric stents. The configuration of the stent may also be chosen from a host of geometries. For example, wire stents can be fastened in a continuous helical pattern, with or without wave-like forms or zigzags in the wire, to form a radially deformable stent. Individual rings or circular members can be linked together such as by struts, sutures, or interlacing or locking of the rings to form a tubular stent. Although a wide variety of distensible members may be used, FIG. 2 shows one particular distensible member 62, a stent, which may be employed in prosthesis 60. The particular stent shown in FIG. 2 is more fully described in commonly assigned U.S. Pat. No. 5,693,085 to Buirge et al. and the disclosure of U.S. Pat. No. 5,693,085 is incorporated by reference herein.

With reference to FIG. 3, an alternative embodiment of the composite graft 60 according to the present invention, is shown therein and designated generally with the reference numeral 60'. Like numbers are used to designate like elements. With this embodiment, an additional inner textile reinforcement 72 is provided which is fixed by an inner layer of bonding agent 74.

The textile layers 68, 72 and the bonding agent layers 70, 74 may be of any structure described in the embodiments above. Likewise, the interaction between the ePTFE layers, the textile layers, and the bonding agent 70, 74 is the same interaction described above.

With either embodiment of the composite graft 60, 60', an implantable prosthesis may be formed which is self-supporting and usable to maintain patency of a bodily vessel, such as in the vasculature, esophagus, trachea, colon, biliary tract, urinary tract, prostate, and brain. Also, the composite graft 60, 60' may be treated with any of the following: anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

Figure 4:
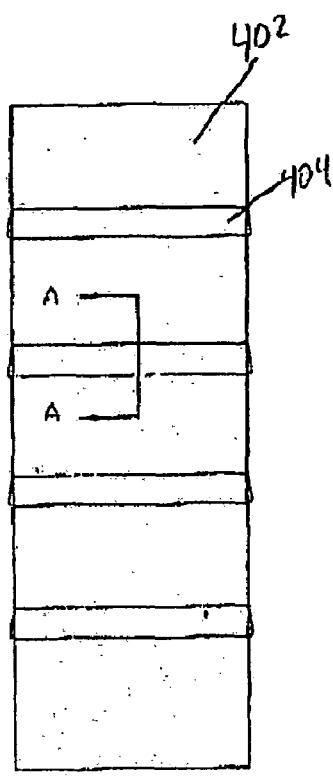
FIG. 4 shows a portion of a pleated composite multi-layered implantable structure of the present invention prior to stretching.

With reference to FIG. 4, a plan view of a pleated section of the composite graft material of the present invention is shown prior to stretching. The depicted section has a top surface 402, having a plurality of pleated regions 404 formed on the top surface of the graft material. The pleated regions are formed by folding the ePTFE material into a flap, which is flattened against the surface of the graft material. The flattened flap creates a region of triple layered ePTFE. The top layer of the ePTFE is covered by the adhesive for bonding the textile layer.

Pleats are incorporated in the material of the present invention along the length of the graft in the manner shown in FIG. 4 so as to control the resultant axial elongation, plastic deformation, longitudinal foreshortening and radial shrinkage of the graft material due to the stresses applied to the graft material by the support structure during the contraction and expansion of the support structure. The length and number of pleats can be varied along the length of the graft in accordance with the expected stress on the graft material from the support structure. Resultant axial elongation, plastic deformation, longitudinal foreshortening and radial shrinkage of the graft material can thus be limited by the application of longer pleats or a greater number of pleats along the length of the graft.

Figure 5:
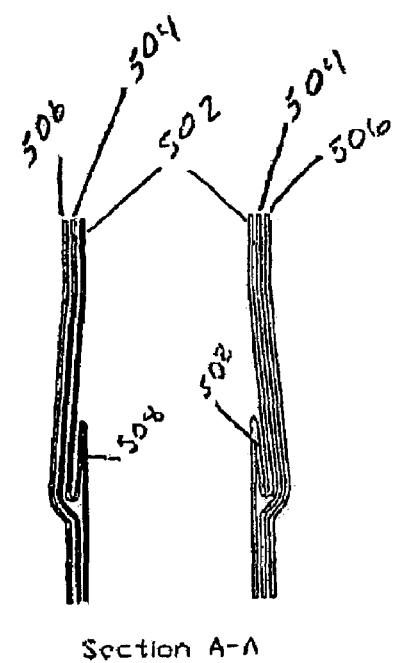
FIG. 5 shows a schematic cross-section of the preferred embodiment of the present invention.

Turning now to FIG. 5, there is shown a cross section view, denoted as section A-A, (as shown in FIG. 4) of the pleated material according to the present invention prior to stretching. In the cross-section there is shown the pleated ePTFE layer 502, an adhesive layer 504 and a textile layer 506. The pleat is formed of a gathered section of ePTFE that is folded substantially flat against the surface of the ePTFE. The surface of the pleated ePTFE layer 502 is coated with an adhesive 504, for bonding the textile layer 506 to the ePTFE layer 502. The pleat masks a portion of the ePTFE layer 508, and prevents the application of adhesive to that masked portion. Because the textile layer does not adhere to the masked portion of the ePTFE layer, the pleated portion can unfold independently of the textile and adhesive layer when the composite device is stretched. Some or all of the elongation produced by the stretching can thus be accommodated by the unfolding of the ePTFE layer. Any elongation in excess of the length added by the pleated regions will result in plastic deformation of the ePTFE layer. However, the plastic deformation can be controlled by varying the number and length of the pleated sections. Increasing the length of the ePTFE material gathered in the pleated sections or the number of pleats, will result in less plastic deformation of the completed device after stretching.

Typically, the material of the present invention would be attached to a support structures. Such as a stent, which are formed of metal or polymeric materials generally formed in a tubular structure and are used to hold a vein or artery open. Stents may be self-expanding or radially expandable by balloon expansion. Typically, a stent graft device is inserted into a delivery system such as a catheter for treatment of the patient. When the stent graft device is inserted into the delivery system it elongates and shrinks in diameter due to the stresses applied to by the stent. The pleated sections, allow the stretching of the ePTFE layer while reducing the plastic deformation of the device when it is stored in the catheter. The ePTFE is pleated to allow a pre-determined amount of dimensional loss to occur.

Figure 6:
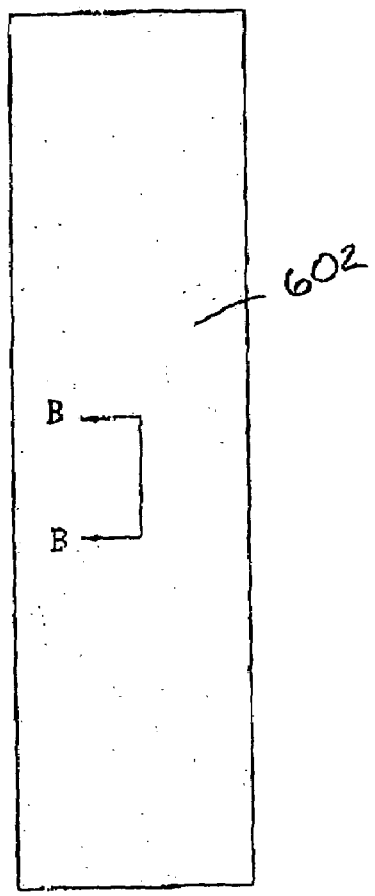
FIG. 6 shows a portion of a pleated composite multi-layered implantable structure of the present invention after stretching.

With reference to FIG. 6, a plan view of a section of the composite graft material of the present invention is shown after stretching. The depicted section has a top surface 602, wherein the flaps of the pleated regions have been unfolded, thereby lengthening the graft material section depicted.

Figure 7:
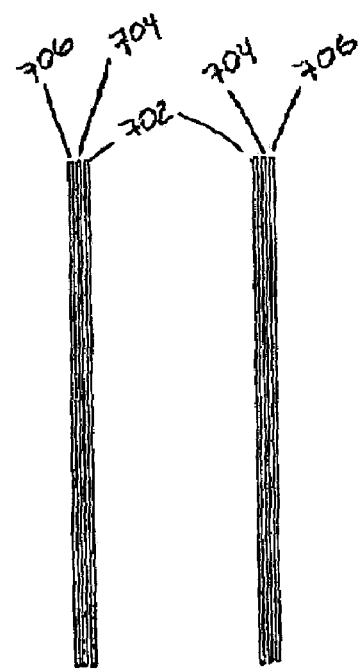
FIG. 7 shows a schematic cross-section of the preferred embodiment of the present invention.

Turning now to FIG. 7, there is shown a cross section view, denoted as section B-B, (as shown in FIG. 6) of the pleated material according to the present invention after stretching. In the cross-section there is shown the ePTFE layer 702 wherein the pleated section has been unfolded, an adhesive layer 704 and a textile layer 706. The masking of the ePTFE layer by the pleated region allows the excess material of the ePTFE layer 702 to unfold into parallel alignment with the textile layer during the stretching of the device. The plastic deformation of the ePTFE layer is therefore controlled by providing excess material that unfolds during stretching. Additionally, due to the excess length of ePTFE material prior to stretching, the percentage of plastic deformation that occurs during the stretching to that layer is reduced.

Figure 8:
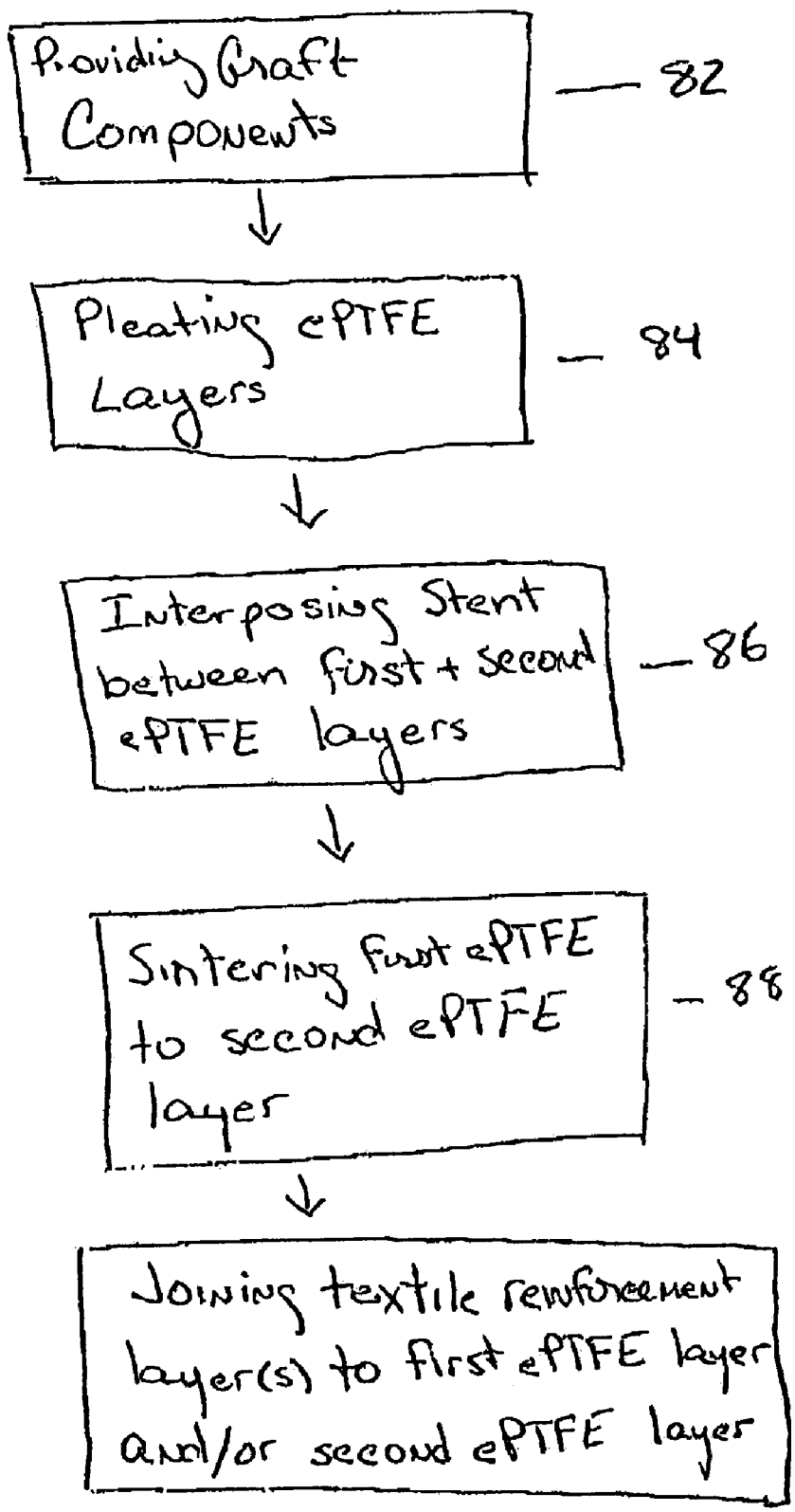
FIG. 8 is a flow chart exemplifying a process for preparing one of the structures of the present invention.

In an exemplary method of forming the composite graft 60, 60', flow chart 80 is presented in FIG. 8. In an initial step 82, components of the composite graft 60, 60' are provided, including the support structure 62; the inner and outer ePTFE layers 64, 66; the textile reinforcement 68 (and, optionally, inner textile reinforcement layer 72); and, bonding agent to form layers 70 and/or 74. The ePTFE layers are pleated in a plurality of locations, step 84. The length and number of pleats are pre-determined based upon the desired amount of expected longitudinal extension. Thereafter, the support structure 62 is interposed between the first and second ePTFE layers 64, 66, for example, on a mandrill, step 86. The ePTFE layers 64 and 66 are sintered together, step 88, so as to bond through the interstices of the support structure 62. The textile layer 68, and, optionally, the textile reinforcement 72, are joined using the layers of bonding agents 70 and 74 in the same process described above with previous embodiments (step 89).

Figure 9:
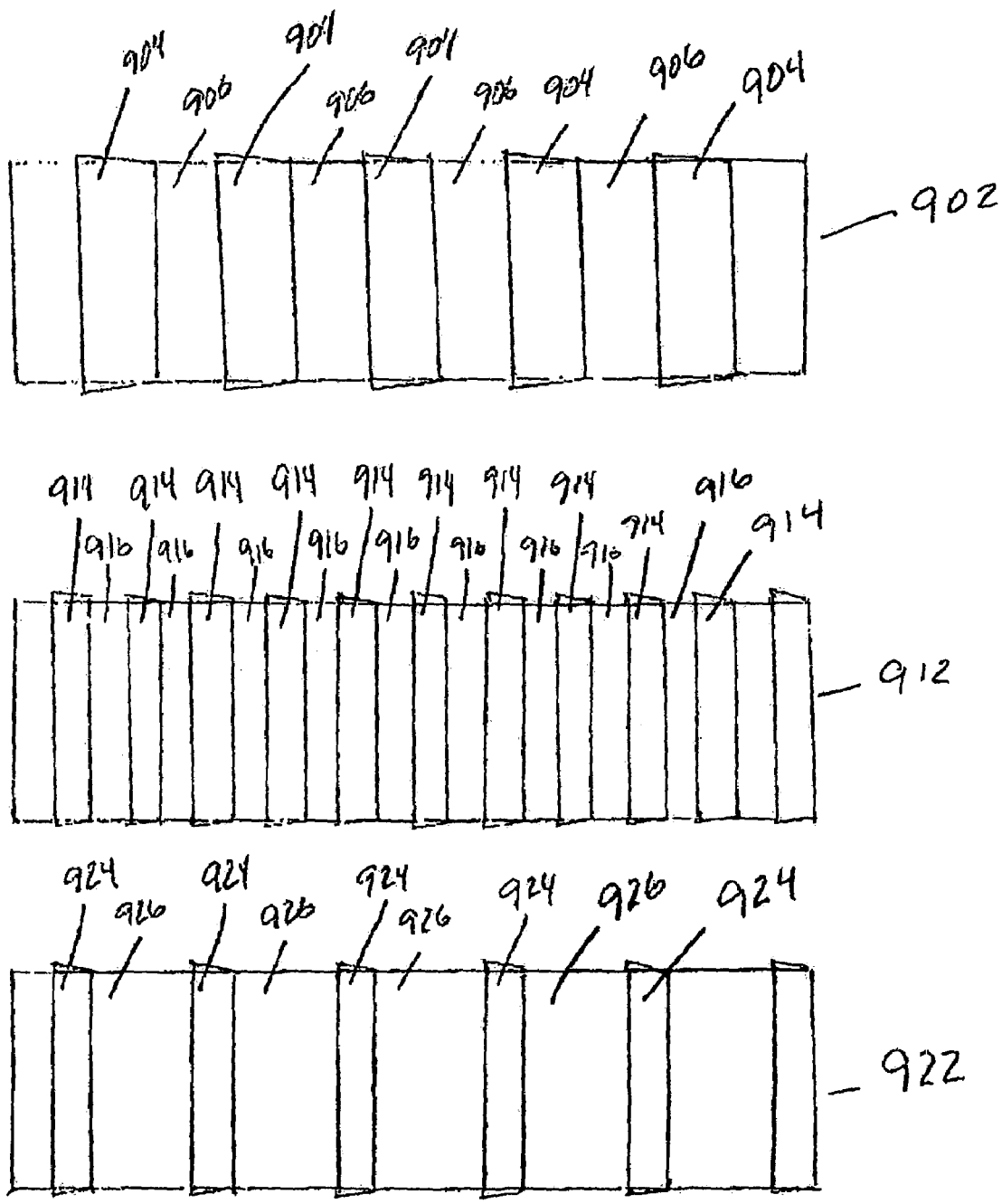
FIG. 9 is an illustration of a graft according to the present invention with varying pleat amplitude and frequency.

It is to be understood that while the exemplified embodiment has been illustrated with specific geometry, a wide variation is possible within the broad teachings of this invention. A few examples of variations of pleating are illustrated in FIG. 9. FIG. 9 shows several of many possible pleated grafts and graft material designs to illustrate that the length and number of the pleats may be varied in order to control the amount of possible longitudinal extension. Depicted in FIG. 9 is: exemplary graft material 902, having pleated regions 904, separated by non-pleated spaces 906, exemplary graft material 912, having pleated regions 914, separated by non-pleated spaces 916 and exemplary graft material 922, having pleated regions 924, separated by non-pleated spaces 926. As can be seen in the exemplary embodiments depicted, the length of the pleated regions as well as the spacing between pleats can be varied. Thus the material properties can be altered to suit the particular application.

The length and number of the pleats may be varied depending on the desired characteristics for a specific graft application. As shown in FIG. 9, several non-limiting variable pleat lengths and numbers are shown in accordance with the present invention. Either the length of pleats, number of pleats or both limitations in combination can control the amount of possible longitudinal extension of the graft. The frequency/length, i.e. number of pleats for a given length may vary, based upon the length of the device as well as the length of the pleats. The length of the pleats may typically be in the range of 0.5 mm to 2 mm. The distance between the pleats may typically be in the range of 5 mm to 20 mm.

Figure 10:
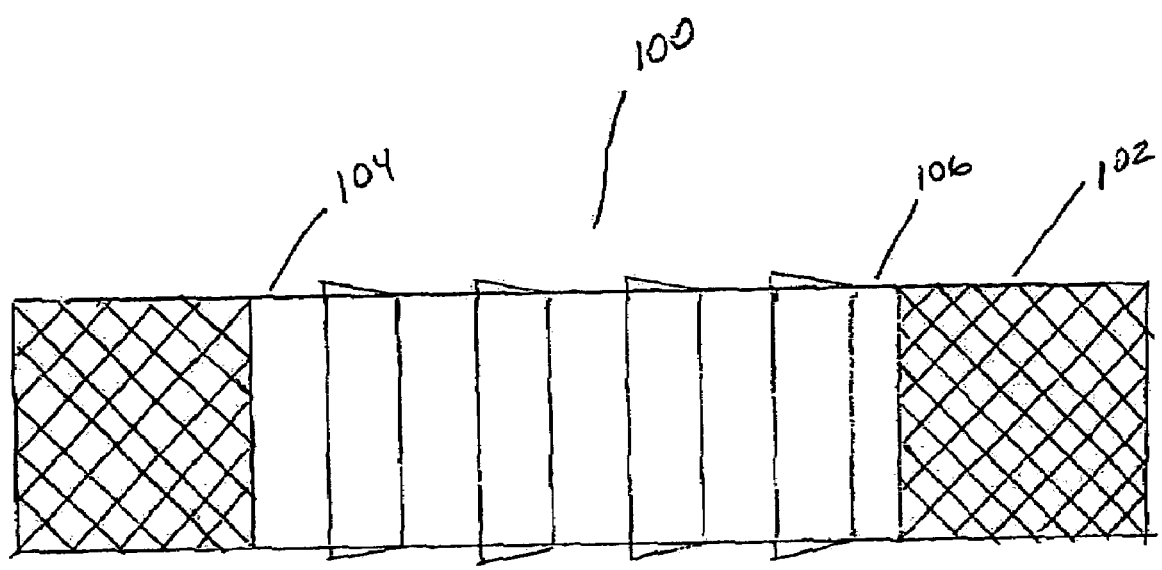
FIG. 10 is an illustration of a stent-graft assembly according to the present invention for implantation within a body lumen.

Referring to FIG. 10, illustrated therein schematically is a stent-graft of the present invention at a preloaded stage for deployment into a vascular vessel. Stent 102 is disposed within and preferably attached to end portions 104 and/or 106 of graft 10. A stent 102 can alternatively be constructed as lining within a graft (not shown) extending from one end of the graft to the other to provide both fastening of the graft to the stent and additionally structural stability.

The pleated graft of the present invention, graft 100, preferably with the end portions 104 and 106 affixed to stent 102, is positioned on a catheter (not shown) to be delivered endoluminally. During delivery or deployment, the stent-graft 100 stretches longitudinally to provide an open lumen and maintains its flexibility. The pleats of the present graft unfold in response to the longitudinal forces produced by the stent device as it is opened, thereby reducing or eliminating the plastic deformation of the ePTFE layer. For example, the graft-stent can be stretched in the axial direction to 175% of its length during loading and when released from the delivery system recover to 125% of it length. The overall length change is 25%. However, if the ePTFE is pleated by 50% and the same axial stretch is applied to the device, the stent and the textile layer would stretch to the 175% length, but the ePTFE would stretch 50% recoverable and 50% unrecoverable which would reduce the recovery length from 125% to 112.5%. Therefore, the material of the present invention does not interfere with the stretching of the textile layer, which is almost fully recoverable, while controlling the stretch of the ePTFE layer to a predetermined amount. Thus, the dimensional change of the device caused by the loading process during delivery can be reduced or eliminated.

Various changes to the foregoing described and shown structures will now be evident to those skilled in the art. Accordingly, the particularly disclosed scope of the invention is set forth in the following claims.

What is claimed is:

1. A composite multilayer implantable material comprising:
   a first inner tubular layer formed of expanded polytetrafluoroethylene having a porous microstructure defined by nodes interconnected by fibrils, wherein said first layer has a plurality of pleated folds, each of said pleated folds forming a masked portion under said pleated folds;
   a second tubular layer formed of textile material circumferentially disposed exteriorly to said first layer, wherein said first and second layers are secured to each other by an elastomeric bonding agent positioned along a contacting layer of said first and second layers; and
   wherein said masked portion of each of said pleated folds is not secured to said second layer by said bonding agent to permit unfolding and longitudinal lengthening of said composite multilayer implantable material.

2. The implantable material of claim 1 wherein said bonding agent is applied to one surface of said first layer.

3. The implantable material of claim 1 wherein said bonding agent is selected from the group consisting of urethanes, styrene/isobutylene/styrene block copolymers, silicones and combinations thereof.

4. The implantable material of claim 1 wherein said second layer comprises a textile pattern selected from the group comprising knits, weaves, stretch-knits, braids, any non-woven process, and combinations thereof.

5. The implantable material of claim 1 wherein said implantable material includes said first layer being a blood contact layer and said second layer being a tissue contacting layer.

6. The implantable material of claim 1 wherein said first, and second tubular layers form an elongate tubular vascular graft.

7. The implantable material of claim 6 wherein said graft includes a plurality of longitudinally spaced crimps thereaong.

8. The implantable material of claim 6 wherein said graft is helically wrapped with a monofilament externally therearound.

9. The implantable material of claim 8 wherein said monofilament comprises polypropylene.

10. The implantable material of claim 9 wherein said monofilament is attached by heat bonding.

11. The implantable material of claim 8 wherein said graft includes an external support coil helically positioned thereover.

12. The implantable material of claim 1 wherein said elastomeric bonding agent is applied, to said second layer in solution.

13. The implantable material of claim 12 wherein said solution includes dimethylacetamide.

14. The implantable material of claim 1, wherein the pleats are of uniform length.

15. The implantable material of claim 1, wherein the pleats have uniform spacing.

16. A composite multilayer implantable structure comprising:
- a first inner tubular layer formed of expanded polytetrafluoroethylene having a porous microstructure defined by nodes interconnected by fibrils;
- a second tubular layer of expanded polytetrafluoroethylene circumferentially disposed exteriorly to said first layer, wherein said first and second layers have a plurality of pleated folds, each of said pleated folds being provided by doubling a continuous portion of said first layer and said second layer upon itself and pressing said continuous portion into an adjacent portion to define a masked portion under each of said pleated folds;
- a support structure positioned between said first and said second layers;
- a third tubular layer formed of textile material circumferentially disposed exteriorly to said second layer; and
- an elastomeric bonding agent applied to one of said second layer or said third layer for securing said second layer to said third layer, wherein said masked portion is not secured to said third tubular layer by said bonding agent to permit unfolding and longitudinal lengthening of said composite multilayer implantable structure.

17. A composite structure of claim 16 wherein said bonding agent is applied to one surface of said first layer.

18. A composite structure of claim 16 wherein said bonding agent is applied to a surface of said third textile layer.

19. A composite structure of claim 16 wherein said bonding agent is selected from the group consisting of urethanes, styrene/isobutylene/styrene block copolymers, silicones and combinations thereof.

20. A composite structure of claim 16 wherein said third layer comprises a textile pattern selected from the group comprising knits, weaves, stretch-knits, braids, any non-woven process, and combinations thereof.

21. A composite structure of claim 16 wherein said third layer is placed in contact with a surface of said second layer.

22. A composite structure of claim 16 wherein said implantable structure includes said first layer being a blood contact layer and said third layer being a tissue contacting layer.

23. A composite structure of claim 16 wherein said first, second and third tubular layers form an elongate tubular vascular graft.

24. A composite structure of claim 23 wherein said graft includes a plurality of longitudinally spaced crimps therealong.

25. A composite structure of claim 23 wherein said graft is helically wrapped with a monofilament externally therearound.

26. A composite structure of claim 25 wherein said graft includes an external support coil helically positioned thereover.

27. A composite structure of claim 23 wherein said monofilament comprises polypropylene.

28. A composite structure of claim 27 wherein said monofilament is attached by heat bonding.

29. A composite structure of claim 16 wherein said elastomeric bonding agent is applied to said second layer in solution.

30. A composite structure of claim 29 wherein said solution includes dimethylacetamide.

31. The implantable material of claim 16, wherein the pleated folds are of uniform length.

32. The implantable material of claim 16, wherein the pleated folds have uniform spacing.

* * * * *